US012758316B2

(12) United States Patent
Srivastava et al.

(10) Patent No.: US 12,758,316 B2
(45) Date of Patent: Oct. 13, 2026

(54) SYSTEM AND METHOD FOR VIRTUAL REALITY TRAINING, SIMULATION OF A VIRTUAL ROBOTIC SURGERY ENVIRONMENT

(71) Applicant: SSI IP HOLDINGS INC., Fort Lauderdale, FL (US)

(72) Inventors: Sudhir Prem Srivastava, Gurugram (IN); Vishwajyoti Pascual Srivastava, Gurugram (IN); S Naveen Ajay Kumar, Gurugram (IN); Atharva Rajesh Madiwale, Gurugram (IN)

(73) Assignee: SSI IP HOLDINGS INC., Fort Lauderdale, FL (US)

( * ) Notice: Subject to any disclaimer, the term of this patent is extended or adjusted under 35 U.S.C. 154(b) by 2 days.

(21) Appl. No.: 18/568,782

(22) PCT Filed: Jun. 9, 2023

(86) PCT No.: PCT/IN2023/050543
§ 371 (c)(1),
(2) Date: Dec. 8, 2023

(87) PCT Pub. No.: WO2023/238157
PCT Pub. Date: Dec. 14, 2023

(65) Prior Publication Data
US 2025/0072968 A1 Mar. 6, 2025

(30) Foreign Application Priority Data
Jun. 10, 2022 (IN) ............................ 202211033296

(51) Int. Cl.
*A61B 34/10* (2016.01)
*A61B 34/00* (2016.01)
(Continued)

(52) U.S. Cl.
CPC .............. *A61B 34/10* (2016.02); *A61B 34/20* (2016.02); *A61B 34/25* (2016.02); *A61B 34/35* (2016.02);
(Continued)

(58) Field of Classification Search
CPC ...... A61B 2034/101; A61B 2034/2046; A61B 2034/2048; A61B 2034/2055;
(Continued)

(56) References Cited

U.S. PATENT DOCUMENTS

2017/0108930 A1* 4/2017 Banerjee ................ A61B 34/72
2019/0133689 A1 5/2019 Johnson et al.
(Continued)

FOREIGN PATENT DOCUMENTS

WO 2020163328 A1 8/2020

OTHER PUBLICATIONS

Rahim, M.S.M. & Norouzi, Alireza & Rehman, A. & Saba, Tanzila. (2017). 3D bones segmentation based on CT images visualization. Biomedical Research (India). 28. 3641-3644.

*Primary Examiner* — Christopher L Cook
(74) *Attorney, Agent, or Firm* — SZDC Law PC

(57) ABSTRACT

The application provides a virtual reality system (200) and a method for simulating a virtual robotic surgery environment for providing training to medical professionals and diagnosis of any anomalies in the diagnostic scan of one or more patients. The virtual reality system (200) comprises an input device (202) configured to receive an input from an operator (204), and a processor (206) coupled to the input device (202) and configured to extract a relevant data (212) based on the received input, from a database (210) stored on a server (208) operably connected to the processor (206), wherein the server (208) is configured to store a database (210) including at least one of a diagnostic scan and patient
(Continued)

details for one or more patients or a virtual tutorial for one or more robotic surgical procedures, render the relevant data (212) on a stereoscopic display (214) coupled to the processor (206), and manipulate the relevant data (212) based on another input received from the operator (204) and render the manipulated data on the stereoscopic display (214), to create a virtual robotic surgery environment.

23 Claims, 9 Drawing Sheets

(51) Int. Cl.

| | |
|---|---|
| ***A61B 34/20*** | (2016.01) |
| ***A61B 34/35*** | (2016.01) |
| ***A61B 90/00*** | (2016.01) |
| ***A61B 90/50*** | (2016.01) |

(52) U.S. Cl.

CPC .............. *A61B 90/36* (2016.02); *A61B 90/50* (2016.02); *A61B 2034/101* (2016.02); *A61B 2034/2046* (2016.02); *A61B 2034/252* (2016.02); *A61B 2034/256* (2016.02); *A61B 2090/365* (2016.02); *A61B 2090/367* (2016.02); *A61B 2090/502* (2016.02)

(58) Field of Classification Search

CPC ........ A61B 2034/252; A61B 2034/256; A61B 2090/365; A61B 2090/367; A61B 2090/502; A61B 34/10; A61B 34/20; A61B 34/25; A61B 34/30; A61B 34/35; A61B 90/36; A61B 90/50; G09B 23/285; A61K 31/706; A61K 45/06

See application file for complete search history.

(56) References Cited

U.S. PATENT DOCUMENTS

2020/0261159 A1* 8/2020 Johnson ................. A61B 34/10
2021/0307831 A1* 10/2021 Fuerst .................. G02B 27/017

* cited by examiner

SYSTEM AND METHOD FOR VIRTUAL REALITY TRAINING, SIMULATION OF A VIRTUAL ROBOTIC SURGERY ENVIRONMENT

CROSS-REFERENCE TO RELATED APPLICATIONS AND PRIORITY

This application is a national sage application of International Application No. PCT/IN2023/050543 filed on Jun. 9, 2023, which application claims priority from Indian patent application Ser. No. 20/221,1033296, filed on Jun. 10, 2022.

TECHNICAL FIELD

The present disclosure generally relates to the field of immersive technology applications in medical devices, and more particularly, the disclosure relates to a virtual reality system for a virtual robotic surgery environment in medical applications.

BACKGROUND

This section is intended to introduce the reader to various aspects of art that may be related to various aspects of the present disclosure, which are described below. This disclosure is believed to be helpful in providing the reader with background information to facilitate a better understanding of the various aspects of the present disclosure. Accordingly, it should be understood that these statements are to be read in this light, and not just as an admissions of prior art.

Robotic assisted surgical systems have been adopted worldwide to gradually replace conventional surgical procedures such as open surgery and laparoscopic surgical procedures. The robotic assisted surgery offers various benefits to a patient during surgery and during post-surgery recovery time. The robotic assisted surgery equally offers numerous benefits to a surgeon in terms of enhancing the surgeon's ability to precisely perform surgery, less fatigue and a magnified clear three-dimensional (3D) vision of a surgical site. Further, in a robotic assisted surgery, the surgeon typically operates with a hand controller/master controller/surgeon input device/joystick at a surgeon console system to seamlessly receive and transfer complex actions performed by him/her giving the perception that he/she himself/herself is directly articulating a surgical tools/surgical instrument to perform the surgery. The surgeon operating on the surgeon console system may be located at a distance from a surgical site or may be located within an operating theatre where the patient is being operated on.

The robotic assisted surgical systems may comprise of multiple robotic arms aiding in conducting robotic assisted surgeries. The robotic assisted surgical system utilizes a sterile adapter/a sterile barrier to separate a non-sterile section of the multiple robotic arms from a mandatory sterile surgical tools/surgical instrument attached to one end of the multiple robotic arms. The sterile adaptor/sterile barrier may include a sterile plastic drape that envelops the multiple robotic arms and the sterile adaptor/sterile barrier that operably engages with the sterile surgical tools/surgical instrument in the sterile field.

For performing robotic assisted surgeries, training is required to be provided to surgeons, operation theater (OT) staff and other assistants, who directly and indirectly participate in these surgeries. One of the main challenges is, unless the surgeon, OT staff and others get completely familiar and trained with all features and functions of the robotic surgical system, performing live surgery is not desirable. Another challenge is, getting familiarity with different features and functions of the robotic surgical system takes its own time. Also, such training requires an ample amount of time investment, creation of training modules, and a physical trainer.

Further, the diagnostic scans of a patient being in 2D format are difficult to manipulate for diagnosing any anomalies. Moreover, the surgeons may face difficulty in identifying the exact position and orientation of an organ during the robotic assisted surgeries.

In light of the aforementioned challenges, there is a need for providing training to the surgeons and OT staff, such that all the issues related to providing training to surgeons and OT staff for performing robotic assisted surgeries are resolved.

SUMMARY OF THE DISCLOSURE

Some or all of the above-mentioned problems related to providing training to the surgeons and OT staff are proposed to be addressed by certain embodiments of the present disclosure.

According to an aspect of the invention, there is disclosed a virtual reality system for simulating a virtual robotic surgery environment comprising one or more virtual robotic arms each coupled to a virtual surgical instrument at its distal end, a virtual operating table, and a virtual patient lying on top of the virtual operating table, whereby the one or more virtual robotic arms are arranged along the virtual operating table, the system comprising: an input device configured to receive an input from an operator; and a processor coupled to the input device and configured to: extract a relevant data based on the received input, from a database stored on a server operably connected to the processor, wherein the server is configured to store a database including at least one of a diagnostic scan and patient details for one or more patients or a virtual tutorial for one or more robotic surgical procedures; render the relevant data on a stereoscopic display coupled to the processor; and manipulate the relevant data based on another input received from the operator and render the manipulated data on the stereoscopic display, to create a virtual robotic surgery environment.

According to another aspect of the invention, there is disclosed a method for simulating a virtual robotic surgery environment comprising one or more virtual robotic arms each coupled to a virtual surgical instrument at its distal end, a virtual operating table, and a virtual patient lying on top of the virtual operating table, whereby the one or more virtual robotic arms are arranged along the virtual operating table, the method comprising: receiving, using an input device, an input from an operator; storing, using a server, in a database at least one of a diagnostic scan and patient details for one or more patients or a virtual tutorial for one or more robotic surgical procedures; extracting, using a processor, a relevant data based on the received input, from the database stored on the server; rendering, using the processor, the relevant data on a stereoscopic display coupled to the processor; manipulating, using the processor, the relevant data based on another input received from an operator; and rendering, using the processor, the manipulated data on the stereoscopic display.

According to an embodiment of the invention, the input device comprises at least one hand controller for each hand or any means to receive hand gestures of the operator.

According to another embodiment of the invention, the input device can be tracked using at least one of an infra-red tracking, optical tracking using image processing, radio frequency tracking, or IMU sensor tracking.

According to yet another embodiment of the invention, the server comprises at least one of a local database or a cloud-based database.

According to yet another embodiment of the invention, each of a diagnostic scan and patient details of one or more patients and a virtual tutorial for one or more robotic surgical procedures comprises of 2D/3D images and texts.

According to yet another embodiment of the invention, the server is further configured to convert a 2D diagnostic scan into a 3D model using a segmentation logic.

According to yet another embodiment of the invention, storing the database including the diagnostic scan and patient details comprises: creating a database of a diagnostic scan and patient details of one or more patients; and modifying the database of one or more patients.

According to yet another embodiment of the invention, the diagnostic scan comprises various medical scans, but not limited to MRI scan, CT scan, and the like, of one or more patients.

According to yet another embodiment of the invention, the patient details comprise at least one of a name, age, sex, or medical history of one or more patients.

According to yet another embodiment of the invention, storing the database including a virtual tutorial for one or more robotic surgical procedures comprises: creating a database of virtual tutorials for one or more robotic surgical procedures using one or more virtual surgical instruments in a virtual robotic surgery environment; and modifying the database of virtual tutorials.

According to yet another embodiment of the invention, the virtual tutorials of one or more robotic surgical procedures can be used to provide training to healthcare professionals.

According to yet another embodiment of the invention, extracting the relevant data from the stored database on the server comprises fetching at least one of a 3D model of diagnostic scan/patient details of one or more patients, or a virtual tutorial for one or more robotic surgical procedures, based on the received input.

According to yet another embodiment of the invention, the relevant data comprises augmented 3D model or a 3D holographic projection, related to at least one of a diagnostic scan and patient details of one or more patients, or a virtual tutorial for one or more robotic surgical procedures.

According to yet another embodiment of the invention, rendering the relevant data comprises displaying the augmented 3D model on a stereoscopic display.

According to yet another embodiment of the invention, the rendered image can be projected on an external display.

According to yet another embodiment of the invention, the stereoscopic display is coupled to a virtual reality headset.

According to yet another embodiment of the invention, the 3D models of diagnostic scan and patient details of one or more patients can be stored on the server for safekeeping and reference.

According to yet another embodiment of the invention, the 3D model of a diagnostic scan can be manipulated to diagnose any anomalies in the diagnostic scan of one or more patients.

According to yet another embodiment of the invention, the 3D models of diagnostic scan and patient details of one or more patients can be used for training healthcare professionals.

According to yet another embodiment of the invention, the manipulated data comprises a modified version of the relevant data, generated based on the received input from the operator.

According to yet another embodiment of the invention, rendering the relevant data of a virtual tutorial for a selected robotic surgical procedure, based on the received input comprises of following steps: positioning of the virtual patient on the virtual operating table; placing of virtual ports on the virtual patient; draping of the virtual robotic arms; docking of the virtual robotic arms in the patient around the virtual operating table; selecting one or more virtual surgical instruments; practicing the selected surgical procedure by using the virtual surgical instruments; undocking and storing the virtual robotic arms; practicing quick undocking of the virtual robotic arms in case of any adverse situation; and cleaning and sterilizing of the virtual surgical instruments post the virtual surgical procedure.

According to yet another embodiment of the invention, the processor is further configured to transmit the manipulated data to the server for storage in the database.

According to yet another embodiment of the invention, the augmented 3D model of the patient anatomy can be superimposed on the virtual patient to enable the surgeon to identify the exact position and orientation of organ during actual surgery.

According to yet another embodiment of the invention, simulating the virtual robotic surgery environment is based on predetermined models for the virtual robotic arms, the virtual surgical instruments, the virtual operating table, and the virtual patient.

According to still another embodiment of the invention, separate sessions of the virtual tutorials for surgeons and OT staff can be designed using the virtual robotic surgery environment.

Other embodiments, systems, methods, apparatus aspects, and features of the invention will become apparent to those skilled in the art from the following detailed description, the accompanying drawings, and the appended claims.

BRIEF DESCRIPTION OF THE DRAWINGS

The summary above, as well as the following detailed description of the disclosure, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein:

FIG. 4(*b*) illustrates an example kidney segmentation model being manipulated by an operator via hand tracking in accordance with an embodiment of the disclosure;

FIG. 4(*c*) illustrates an example heart segmentation holographic model projected on a magnetic resonance imaging (MRI) scan in accordance with an embodiment of the disclosure;

FIG. 6(*b*) illustrates an example simulated view of 3D model of a virtual heart being manipulated by a surgeon using hand controllers in accordance with an embodiment of the disclosure;

DETAILED DESCRIPTION OF THE DISCLOSURE

Figure 1:
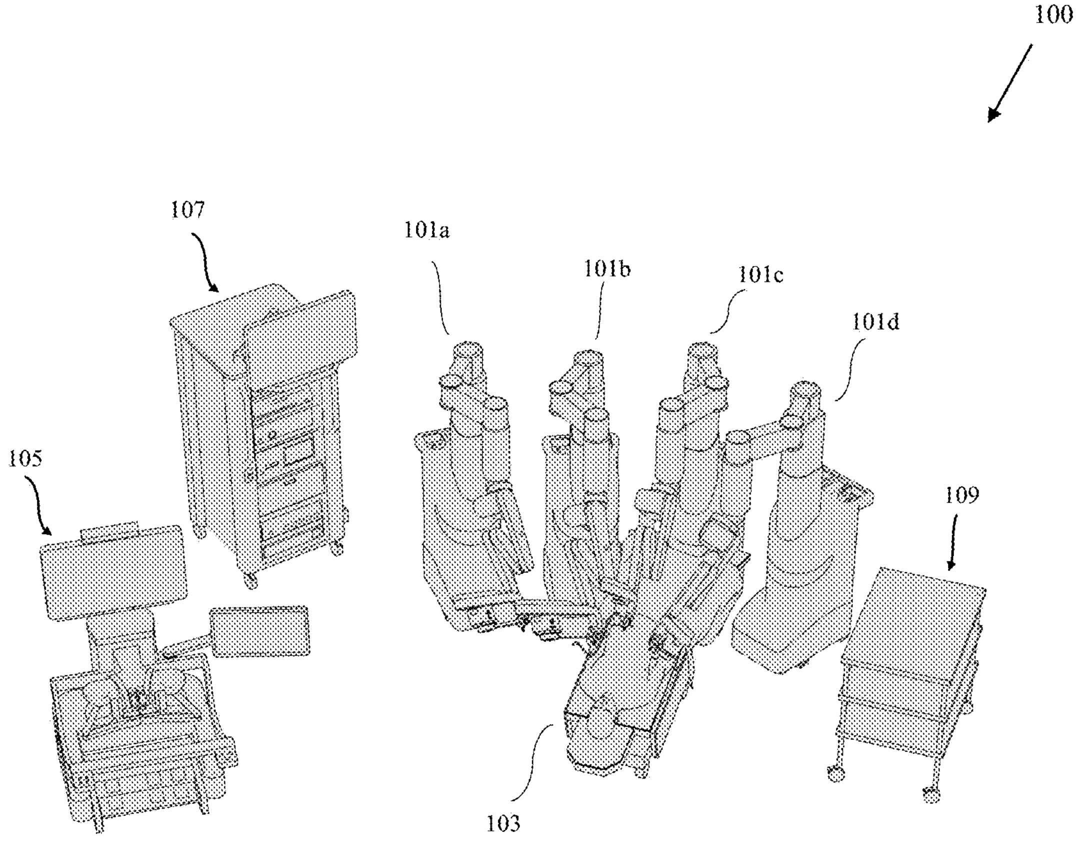
FIG. 1 illustrates an example implementation of a multi arm teleoperated surgical system which can be used with one or more features in accordance with an embodiment of the disclosure.

For the purpose of promoting an understanding of the principles of the disclosure, reference will now be made to the embodiment illustrated in the drawings and specific language will be used to describe the same. It will nevertheless be understood that no limitation of the scope of the disclosure is thereby intended, such alterations and further modifications in the illustrated system, and such further applications of the principles of the disclosure as illustrated therein being contemplated as would normally occur to one skilled in the art to which the disclosure relates.

It will be understood by those skilled in the art that the foregoing general description and the following detailed description are exemplary and explanatory of the disclosure and are not intended to be restrictive thereof. Throughout the patent specification, a convention employed is that in the appended drawings, like numerals denote like components.

Reference throughout this specification to "an embodiment", "another embodiment", "an implementation", "another implementation" or similar language means that a particular feature, structure, or characteristic described in connection with the embodiment is included in at least one embodiment of the present disclosure. Thus, appearances of the phrase "in an embodiment", "in another embodiment", "in one implementation", "in another implementation", and similar language throughout this specification may, but do not necessarily, all refer to the same embodiment.

The terms "comprises", "comprising", or any other variations thereof, are intended to cover a non-exclusive inclusion, such that a process or method that comprises a list of steps does not include only those steps but may include other steps not expressly listed or inherent to such process or method. Similarly, one or more devices or sub-systems or elements or structures proceeded by "comprises . . . a" does not, without more constraints, preclude the existence of other devices or other sub-systems or other elements or other structures or additional devices or additional sub-systems or additional elements or additional structures.

Unless otherwise defined, all technical and scientific terms used herein have the same meaning as commonly understood by one of ordinary skill in the art to which this disclosure belongs. The device, system, and examples provided herein are illustrative only and not intended to be limiting.

The terms "a" and "an" herein do not denote a limitation of quantity, but rather denote the presence of at least one of the referenced items. Further, the term sterile barrier and sterile adapter denotes the same meaning and may be used interchangeably throughout the description.

Embodiments of the disclosure will be described below in detail with reference to the accompanying drawings.

FIG. 1 illustrates an example implementation of a multi arm teleoperated surgical system which can be used with one or more features in accordance with an embodiment of the disclosure. Specifically, FIG. 1 illustrates the multi arm teleoperated surgical system (100) having four robotic arms (101*a*), (101*b*), (101*c*), (101*d*) mounted on four robotic arm carts around an operating table (103). The four-robotic arms (101*a*), (101*b*), (101*c*), (101*d*) as depicted in FIG. 1 are for illustration purposes and the number of robotic arms may vary depending upon the type of surgery. The four robotic arms (101*a*), (101*b*), (101*c*), (101*d*) are arranged along the operating table (103) and may also be arranged in different manner but not limited to the robotic arms (101*a*), (101*b*), (101*c*), (101*d*) arranged along the operating table (103). The robotic arms (101*a*), (101*b*), (101*c*), (101*d*) may be separately mounted on the four robotic arm carts or the robotic arms (101*a*), (101*b*), (101*c*), (101*d*) mechanically and/or electronically connected with each other or the robotic arms (101*a*), (101*b*), (101*c*), (101*d*) connected to a central body (not shown) such that the robotic arms (101*a*), (101*b*), (101*c*), (101*d*) branch out of a central body (not shown). Further, the multi arm teleoperated surgical system (100) may include a console system (105), a vision cart (107), and a surgical instrument, accessory table (109). Further, the robotic surgical system may include other suitable equipments for supporting functionality of the robotic components.

Also, the surgeon/operator may be based at a remote location. Then the console system (105) may be located in any room other than the robotic surgery environment, or the console system (105) may be operated from a remote location. The communication between the console system (105) and the robotic surgical system (100) may be either wired or wireless and may be implemented. The surgeons and OT staff/other assistants are required to be trained to perform these robotic assisted surgeries.

Further, the medical sector relies heavily on diagnostic scans not limited to computerized tomography (CT) and magnetic resonance imaging (MRI) scans for diagnosis. The CT and MRI scans allow the doctors to analyze and study the internal parts of the body. The doctors and surgeons rely upon CT and MRI scans to help diagnose tumors and internal bleeding or check for internal damage. The CT and MRI scans are extremely important during surgical procedures as well. The CT scans show bones and organs, as well as detailed anatomy of glands and blood vessels. The CT scans are taken shortly before surgery to confirm the location of a tumor and establish the location of the internal organs. The CT and MRI scans are essentially a two-dimensional (2D) medium of information. The patient details comprise at least one of a name, age, sex, or medical history of one or more patients. These patient details of one or more patients and the virtual tutorial for one or more robotic surgical procedures comprise of 2D/3D images and texts. Due to the inherent 2D nature of the diagnostic scans, it is sometimes difficult to visualize a particular organ or tumor in 3D. For example, it is very difficult to visualize a tumor just by looking at the MRI scans. Further, it is difficult to visualize its size, orientation, and other characteristic traits.

A virtual reality system may be of great use in providing training to medical healthcare professionals, performing collaborative long-distance surgeries, and diagnosis of any anomalies in the diagnostic scan of one or more patients.

Figure 2:
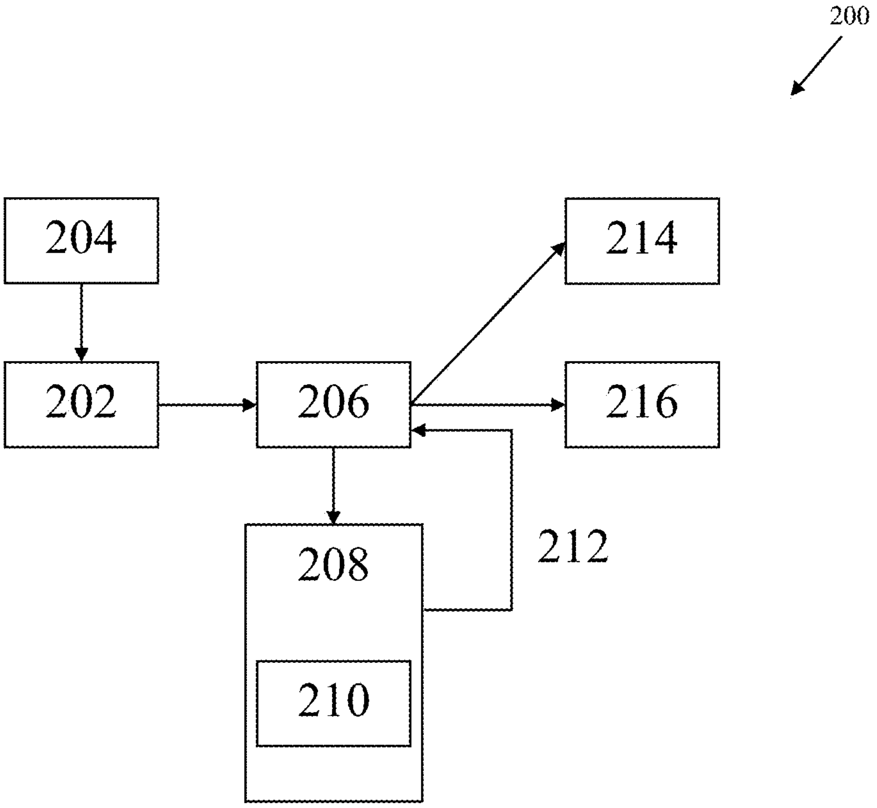
FIG. 2 illustrates a virtual reality system in accordance with an embodiment of the disclosure.

A virtual reality system for simulating a virtual robotic surgery environment is described herein. A virtual reality system (200) is illustrated in FIG. 2. The virtual reality system (200) may include an input device (202) to receive input from an operator (204). The input device (202) comprises at least one hand controller for each hand or any means to receive hand gestures of the operator (204). The input device (202) can be tracked using at least one of an infra-red tracking, optical tracking using image processing, radio frequency tracking, or IMU sensor tracking. The input device (202) is coupled to a processor (206). A server (208) is designed to store a database (210) comprising at least one of a local database or a cloud-based database. The database (210) including patient details of one or more patients, patient related diagnostic scans, and virtual tutorials for one or more robotic surgical procedures, is created in the server (208). Further, the database (210) can be modified based on requirement. The virtual tutorials of one or more robotic surgical procedures can be used to provide training to medical healthcare professionals. The server (208) is further configured to convert a 2D diagnostic scan and patient details into a 3D model using a segmentation logic. These 3D models can be stored on the server (208) for safekeeping and reference.

The processor (206) is configured to extract a relevant data (212) from the server (208) based on the received input from the operator (204). The relevant data (212) comprises at least one of a 3D model of diagnostic scan and patient details of one or more patients, or a virtual tutorial for one or more robotic surgical procedures, based on the received input. The processor (206) then renders the relevant data (212) on a stereoscopic display (214). The relevant data (212) can be an augmented 3D model or a 3D holographic projection.

An external display (216) may be provided to display the relevant data (212). The external display (216) is adapted to display the virtual robotic surgery environment. The stereoscopic display (212) and the external display (214) may be in sync, to be able to display the same content. The stereoscopic display (212) can be coupled to a virtual reality headset.

Figure 3:
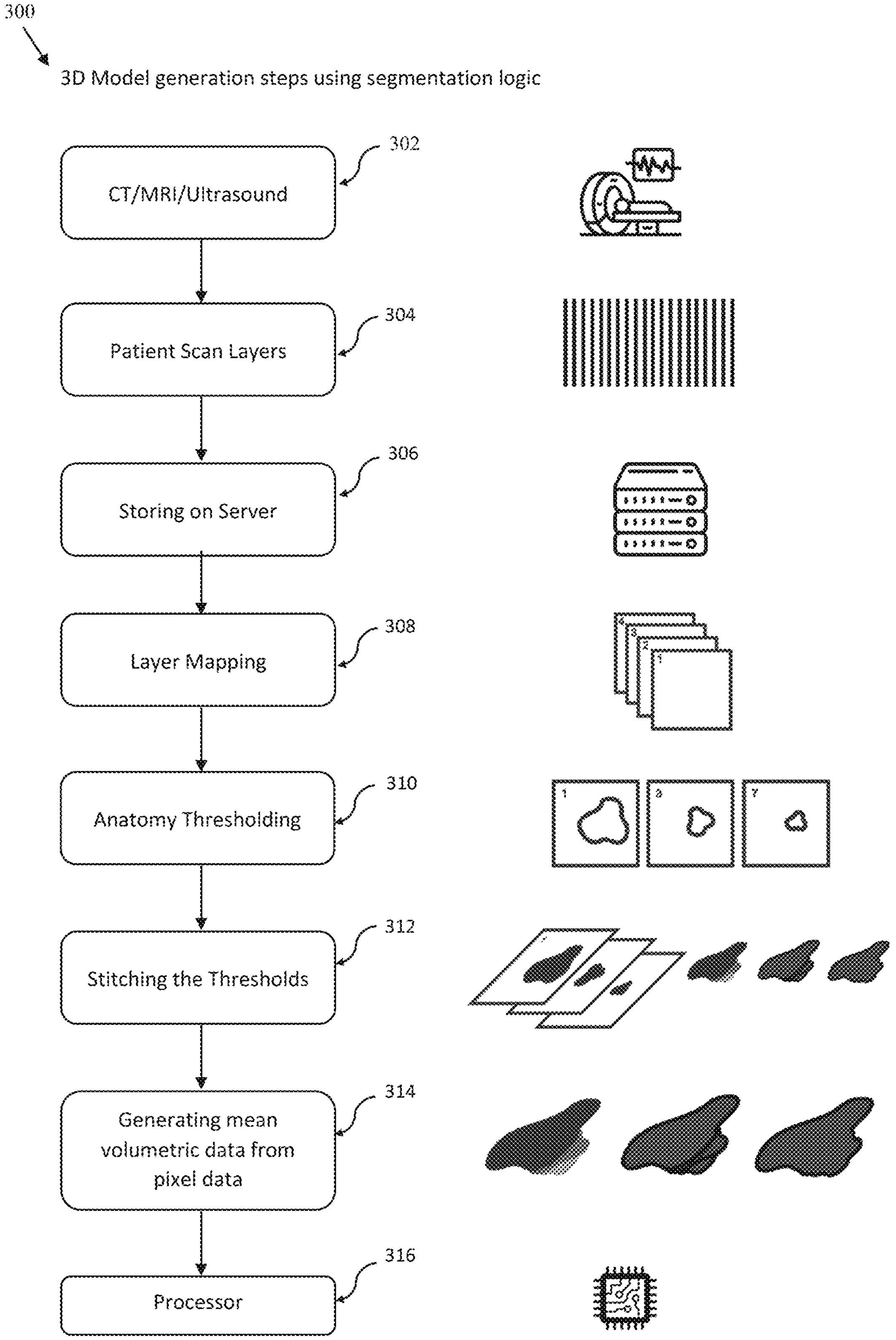
FIG. 3 illustrates a flowchart of steps followed for generation of 3D model using segmentation logic in accordance with an embodiment of the disclosure.

FIG. 3 illustrates a flowchart of steps followed for generation of 3D model using segmentation logic. The database (210) stored in the server (208) is segmented using the logic as performed in following steps: In step (302), the Patient is recommended to get a CT/MRI/Ultrasound scan by the doctor for diagnostic purposes. The CT/MRI/Ultrasound machines scan the patient layer by layer with a certain layer thickness for different scan resolutions in step (304). These Layers are exported as digital files with the DICOM extension and stored in a server's database being indicated in step (306). In step (308), the DICOM files are processed by the server by mapping the layers into correct sequences. Further, based on the received input from the operator, about the anatomy of interest, the anatomical structures of the DICOM layers are given contours by thresholding the pixel values into a certain range. In this process the outlines of the margin of the anatomy of interest are traced in step (310). These traced outlines or thresholds are then stacked in step (312) according to the layer mapping process of step (308) and the 2D outlines are defined into 3D by stacking. In step (314), the stacking data of the thresholds are given an average value of 3D construction and a volumetric data is generated based on the pixel data. Then, the anatomy is converted into a 3D model. Based on the received input from the operator (204), the relevant data (212) (which is a 3D model) is extracted by the processor (206) from the server (208) for further processing.

The processor (206) renders these 3D models using the stereoscopic display (214) or external display (216). These 3D models can also be viewed through virtual reality headsets for viewing the MRI/CT models in 3D. The processor (206) manipulates the relevant data (212) based on further inputs received from the operator (204) and renders the manipulated data on the stereoscopic display (214) or external display (216). The manipulated data comprises of a modified version of the relevant data (212), based on the received input from the operator (204). The manipulation of 3D relevant data (212) helps in diagnosing any anomalies in the diagnostic scan of a one or more patients.

Figure 4A:
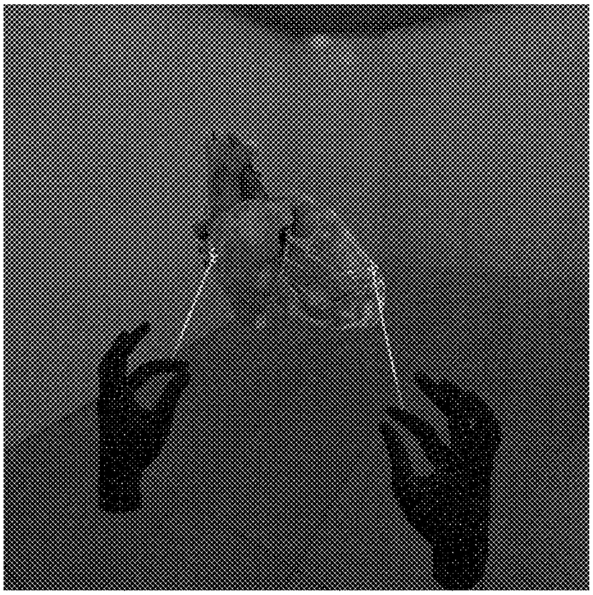
FIG. 4(*a*) illustrates an example heart segmentation model being manipulated by an operator via hand tracking in accordance with an embodiment of the disclosure.
Figure 4B:
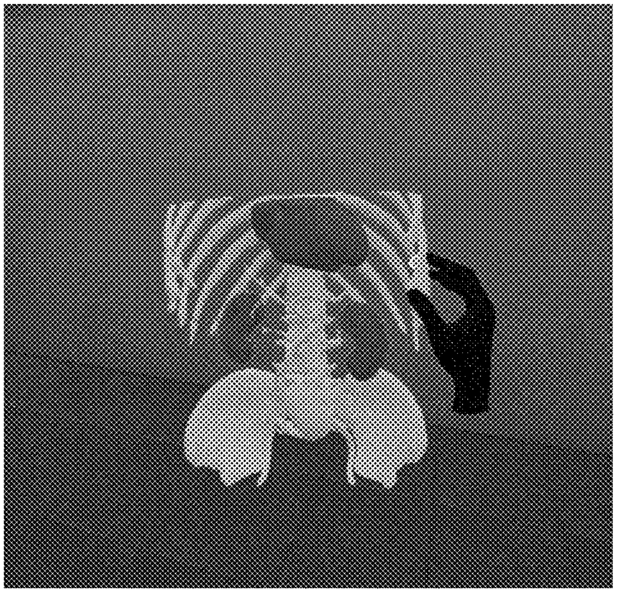
Figure 4C:
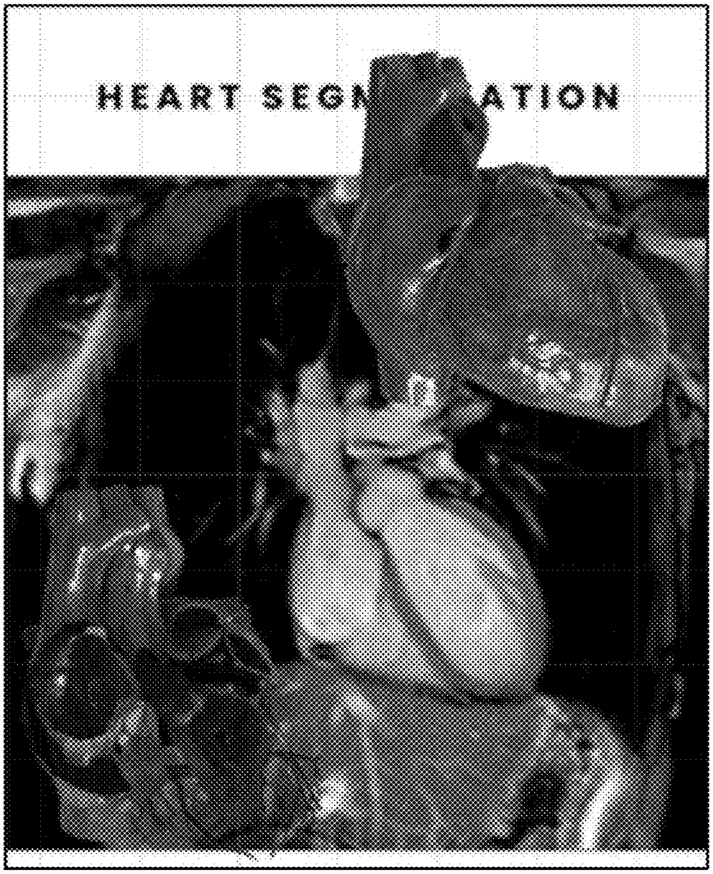

FIG. 4(*a*) illustrates an example heart segmentation model being manipulated by an operator via hand tracking in accordance with an embodiment of the disclosure and FIG. 4(*b*) illustrates an example kidney segmentation model being manipulated by the operator via hand tracking in accordance with an embodiment of the disclosure. The 3 main types of simulated/digital realities can be virtual reality, augmented reality, and mixed reality. The virtual reality is a simulated environment that is independent of the actual surroundings around the operator. The operator may wear a virtual reality headset that provides the operator with a completely immersive experience. A simulated world is projected in virtual reality lenses which is substantially cut off and independent from the real world and environment. The advantage of having a virtual reality simulation is that an extended reality operator has control over all the aspects of the environment. The surroundings, holographic projections, and the interactions the operator can have with these holographic projections can be determined and controlled by the extended reality operator. The virtual reality is an immersive experience which may give the operator a feeling as if he/she is present in the simulated environment.

The operator (204) now has the freedom to enlarge the 3D model, filter out the unwanted parts and focus on the organ of interest. The operator (204) can study the internal structure of the organ by either enlarging it or slicing the 3D hologram to view the internal structure. The 3D visualization will not only help doctors/surgeons in conducting diagnoses but also can be further used for training purposes. They will have the freedom to manipulate these 3D holographic projections in any way they want. They can move, rotate the holographic projections, and adjust the scale of the holographic projection. The created database (210) will contain all the 3D scans of the patient for safekeeping and reference. Whenever needed, the scans of a particular patient can be accessed and referred to.

FIG. 4(*c*) illustrates an example heart segmentation holographic model projected on a magnetic resonance imaging (MRI) scan in accordance with an embodiment of the disclosure. Any segmentation 3D model can be manipulated by the surgeon to get a better understanding of the anatomy of the patient. As these holographic projections are segmented from the MRI scan of the patient itself, the structural characteristics of the organ, its shape, size, and orientation perfectly match the actual organ of the patient.

Figure 5:
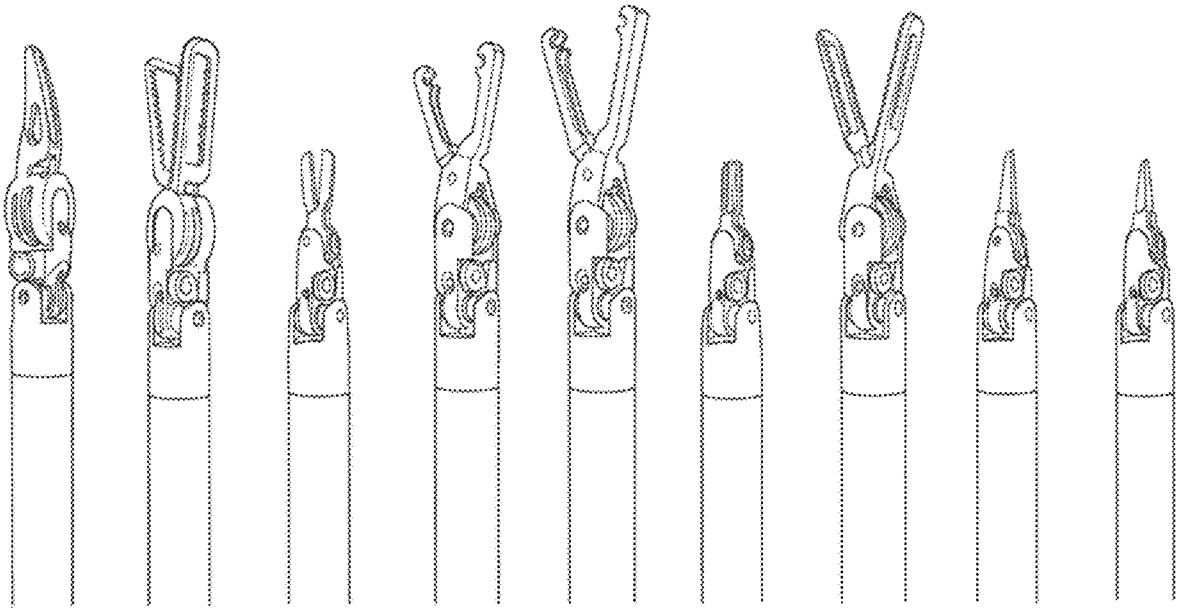
FIG. 5 illustrates tracking of various virtual robotic surgical instruments in accordance with an embodiment of the disclosure.

FIG. 5 illustrates various virtual robotic surgical instruments to be utilized in one or more robotic surgical procedures, in accordance with an embodiment of the disclosure. In an embodiment, image processing techniques may be used for surgical instruments tracking. Using model target recognition in image processing techniques, the application will be able to identify and track the various surgical instruments that are used during surgery. Once image processing techniques recognize the instrument, it will superimpose a holographic projection of the instrument on top of the actual instrument. Thereafter, the position and orientation of the surgical instrument will be tracked, and the OT staff will be able to see the exact position and orientation of the instrument, even if the instrument is inserted in the patient.

Another type of immersive technology is the augmented reality. In the augmented reality, holographic projections are placed while keeping the surroundings the same as the actual one. Yet another type of immersive technology is the mixed reality. The mixed reality is the merging of real and virtual worlds to produce new environments and visualizations, where physical and digital objects co-exist and interact in real time. The holographic projections interact with the surroundings and the object in them. For example, in mixed reality, a holographic object can be placed on a table as an actual object. It will recognize the table as a solid body and will not pass through it. In mixed reality, the holographic projections and the surroundings are interdependent. It makes holograms interactive that co-exist with the surroundings. The extended reality platform may include virtual reality, mixed reality, and augmented reality. The virtual reality headset can be Oculus Quest 2 and mixed reality headset can be Microsoft HoloLens.

Figure 6A:
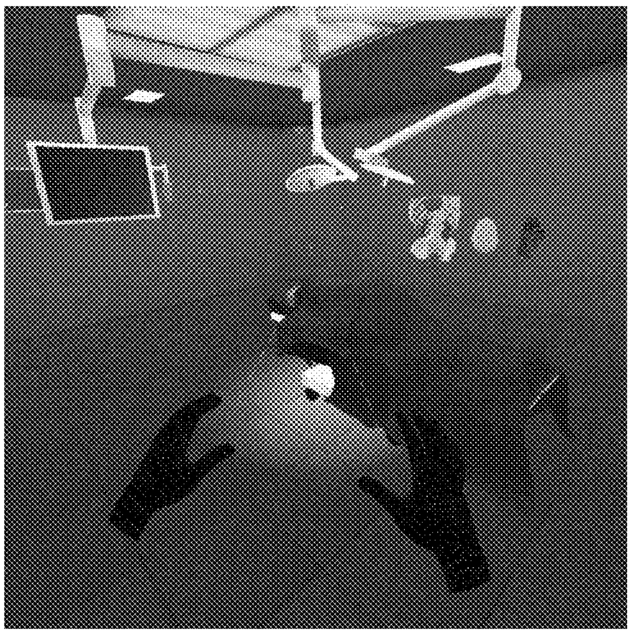
FIG. 6(*a*) illustrates the virtual robotic surgery environment containing segmentation models of the heart, kidney, and brain in accordance with an embodiment of the disclosure.
Figure 6B:
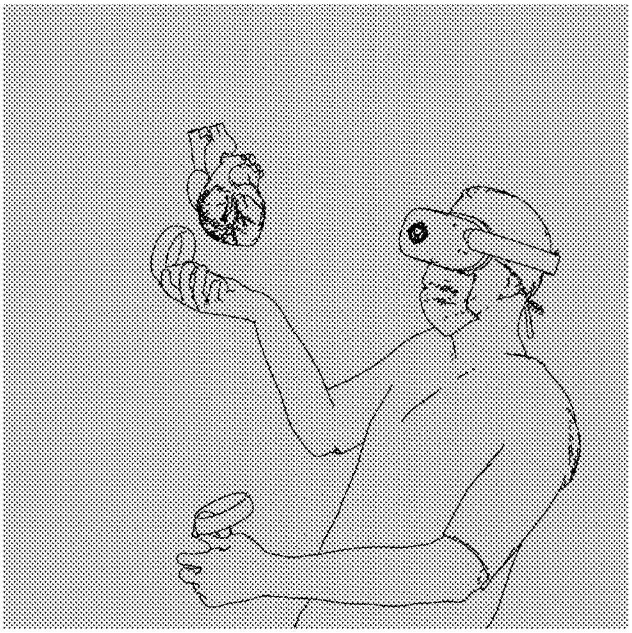

FIG. 6(*a*) illustrates an example simulated view of a virtual robotic surgery environment in accordance with an embodiment of the disclosure. As illustrated in FIG. 6(*a*), the simulated virtual robotic surgery environment contains segmentation models of the heart, kidney, and brain. All 3 models are derived from the DICOM files of the patient. The hand gestures of the operator can be utilized to simulate the virtual robotic surgery environment. FIG. 6(*b*) illustrates an example simulated view of a 3D model of a virtual heart being manipulated by a surgeon using hand controllers in accordance with an embodiment of the disclosure.

In an embodiment, a simulator may be used to get the surgeons and OT staff to get accustomed with various procedural and structural aspects of robotic surgery. The surgeons and OT staff should develop muscle memory when it comes to setting up the robotic surgical system. In one embodiment, the simulator will have training modules specifically for surgeon console, vision cart and patient cart placement techniques. The simulator will go step-by-step and teach the surgeons and OT staff the method and process of placement for all the 3 components. The simulated sessions will be designed in such a way that an entire surgical procedure will be simulated, and the doctors/surgeons will receive step-by-step instructions on all the activities conducted during the surgery. There may be separate tutorials for surgeons and the OT staff. As the tasks being performed by them will be different, they will receive separate as well as common training modules that will guide them to perform tasks in parallel. This way, during an actual surgical procedure, the OT staff and the surgeon will be able to perform their respective tasks collaboratively and smoothly.

Figure 7:
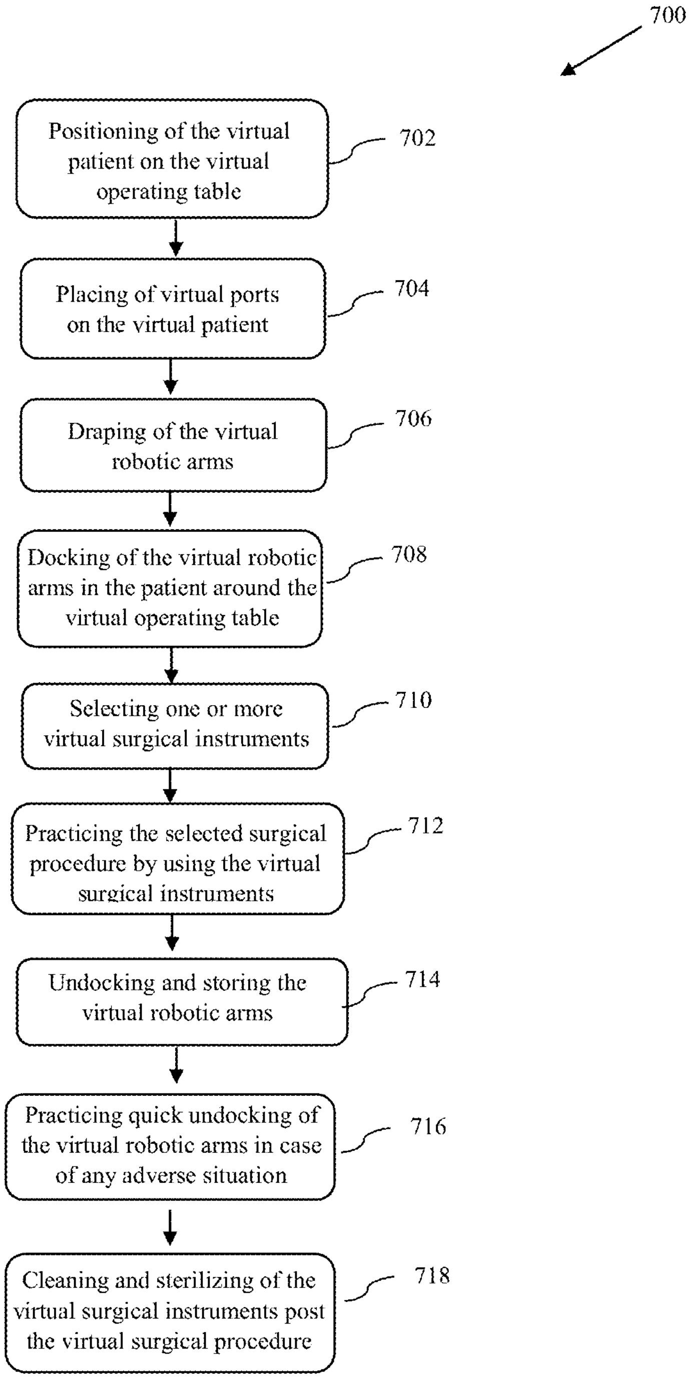
FIG. 7 illustrates the training steps in accordance with an embodiment of the disclosure.

The layout of the tutorials may be segregated into various steps. For example, the first step may be selection of the surgery. As each of the tutorial sessions will be surgery specific, the surgeons and OT staff will be given the option to select the surgery. Based on this selection, the rest of the surgical training sessions will be selected. FIG. 7 illustrates the training steps (700) of a virtual tutorial in accordance with an embodiment of this disclosure. After selection of the surgery, the positioning of the virtual patient on the virtual operating table is carried out in step (702). Based on the virtual surgical procedure being conducted, the virtual patient's position may be decided. The surgeons and OT staff may have to prepare the virtual patient by positioning him/her according to the type of virtual surgical procedure. In step (704), the placing of virtual ports on the virtual patient is carried out. In port placement procedure, based on the type of surgery and organ of interest, ports are placed at specific locations. Port placement assistance can be provided at the initial stages, but once the OT staff are thorough with the process, they can complete this process without assistance. As a part of the port placement training module, the surgeons and OT staff will be trained for trocar placements and final cannula placements.

In the next step (706), the virtual robotic arms and virtual patient cart are draped. The entire draping procedure can be explained in detail. The robot needs to be placed in the draping position. The OT staff will be taken through a simulated draping process in which they will have to perform the entire draping procedure for each arm. As a warning, pop-ups alerts/messages may be provided that highlight the possible places where the drape might potentially get stuck and tear. The OT staff will take into consideration all the guidelines and complete the draping procedure accordingly.

In the next step (708), the placement and docking of the virtual robotic arms in the virtual patient around the virtual operating table is done. The placement of the patient cart is surgery specific. Patient positioning also needs to be considered. The surgeons and OT staff will be taken through the entire process of virtual patient cart placement with step-by-step guidelines. The best practices and ideal steps will be displayed, and the OT staff will be trained. Then, they can practice by placing and docking the virtual patient carts in their respective locations and orientations based on the type of selected virtual surgical procedure and port placement.

The next step (710) is selection and placement of virtual surgical instruments. The selection and preparation of a virtual surgical instrument is done based on the selected surgical procedure. In this session, the OT staff and surgeons can select the virtual instruments that will be used during the selected virtual surgical procedure. Once the selection process is completed, they can practice handling and placement of virtual surgical instruments on the virtual robotic arms in step (712). By repeated practice of virtual instrument placement and removal, the surgeon/OT staff will develop muscle memory of the entire process and will find the placement and removal of the actual physical instruments easier.

The step (714) involves undocking and storage of the virtual robotic arms. Once the training session of the intra-operative procedure ends, the post-operative training session will include undocking and storage of virtual robotic arms. The surgeons and OT staff will be taken through the steps that are required to safely undock the patient cart arms. They will have a checklist type assistance that will highlight the steps they need to perform to undock the system. Next in step (716), as a contingency step, the OT staff and the surgeons also need to be trained on quickly undocking the virtual robotic arms in any adverse situation. For the surgery to be quickly converted, the surgeons and OT staff will be trained in a way that they can quickly react and perform the appropriate steps seamlessly to ensure patient safety.

Next step (718) will be cleaning and sterilization of virtual surgical instruments. Post-surgery, the surgical instruments undergo a thorough cleaning and sterilization process. This session will take the surgeons and OT staff through the process of cleaning and sterilizing the surgical instrument properly. They will be taken through each step one by one after which they will be able to properly clean and sanitize actual surgical instruments after an actual robotic surgery. Autoclaving procedure steps will also be explained, and practice runs will be conducted.

In one embodiment, once the virtual robotic arms of the virtual surgical system are undocked, they will be taken through the steps for the proper storage of the entire robotic surgical system. They can practice undocking and storage procedures to get used to the system in step (716). The troubleshooting and conversion of surgery is achieved.

In an embodiment, the application of mixed reality for intra-operative procedures is described. The CT scans and MRI scans (DICOM files) can be converted into a 3D model. Using various segmentation techniques, the organ of interest can be segmented from the entire CT/MRI scan and converted into a 3D model. This 3D model can then be superimposed on the patient to give the surgeon a 3D view of the patient's anatomy and organ of interest. This will ensure the surgeon always knows the exact position and orientation of the organ. The mixed reality headset can identify an MRI scan image target using any image processing techniques and project the appropriate holographic model. This model can then be superimposed on the patient to find out the exact location and orientation of the organ of interest. The holographic projection of the organ of interest will have the exact size, anatomical structure, and characteristics of the patient's organ as it has been converted from his/her own MRI or CT scan.

In an embodiment, the mixed reality headset identifies the MRI scan as an image target and deploys the 3D holographic model on top of it. Once the model is deployed, the surgeon can manipulate this hologram and superimpose it on the patient on a 1:1 scale. As illustrated in FIG. 4(*c*), the upper portion is the complete heart structure converted from an MRI scan. The lower section is a cut-out section of the heart. The green dye is used for an imaging technique called fluorescence imaging. To help visualize the biological processes taking place in a living organism, a non-invasive imaging technique known as fluorescence imaging may be used. A dye is injected into the patient, and when seen under fluorescent light, highlights the areas that have secreted the dye. This procedure is used for cancer cell detection in lymph nodes.

In one embodiment, the OT staff also rely on the vision cart 3D screen to view the feed of the endoscope. With help of mixed reality glasses, the feed from the endoscope can be directly relayed on a virtual screen that they can place anywhere they think is comfortable. The main purpose of the virtual screen will be to reduce the neck strain and visibility issues that occur because of looking at the vision cart screen for prolonged periods of time. The virtual screen will display the 3D view from the endoscope that will ensure the OT staff have the same view as the surgeon.

In an embodiment, application of mixed reality for surgical instrument assistance is described. The robotic surgical systems may have multiple endoscopic surgical instruments that are operated during a surgical procedure. These surgical instruments are inserted into the patient's body via cannulas. Each surgical instrument performs a unique function. There are multiple types of surgical instruments available such as energy instruments which may include monopolar instruments, bipolar instruments, and harmonic instruments. These instruments come under electrosurgical instruments. The electrosurgery is the application of a high-frequency alternating polarity, and electrical current on a biological tissue to cut, coagulate, desiccate, or fulgurate tissue. Its benefits include the ability to make precise cuts with limited blood loss. Monopolar, bipolar, and harmonic are the 3 types of instruments used. In monopolar instruments, energy is passed from one jaw of the instrument to a grounding pad attached to the patient via the tissue. The tissue is then either cut or coagulated when energy is passed. In bipolar instruments, the energy is passed from one jaw of the instrument to the other via the tissue. The tissue is held between the 2 jaws, and energy is passed. Harmonic instruments make use of ultrasonic vibrations to cut a tissue faster. Harmonic instruments are essentially bipolar instruments in which the 2nd passes ultrasonic vibrations through the tissue to cut it faster.

All the surgical instruments have a unique number of maximum uses. Once the number of maximum uses is over, the instrument is no longer detected by the robotic surgical system. To ensure proper bifurcation of instruments, each instrument has a unique serial number as well. In one embodiment, a unique information related to a particular virtual surgical instrument may be displayed on top of the virtual surgical instrument when selected by the operator (204) using either hand gestures/hand controllers (202). The surgical instruments that are required during a surgical procedure are prepped before the actual surgery as a pre-operative procedure. Having a checklist for all instruments, and having unique IDs, names and types are very difficult to manage. It is impractical for the OT staff to know the names, types, and other important information of various separate instruments.

In an embodiment, when the surgeon/OT staff selects a virtual surgical instrument, all the important information will be displayed over the virtual surgical instrument in the form of a text box. This information can be used to confirm the instruments being prepped for surgery are the required instruments, and that they are not expired instruments. The mixed reality headset will identify the unique ID on the selected virtual surgical instrument and based on that will gather related data from database (210) stored on the server (208). This information will then be displayed over the virtual surgical instrument. The project model needs to have the capability to be able to detect multiple virtual surgical instruments at the same time and display the correct information on top of the respective virtual surgical instrument.

In an embodiment, the integration of extended reality headsets will not only assist surgeons and OT staff in their procedures but also ensure maximum safety for patients. Having interactive holograms responding to their environments will assist OT staff and surgeons immensely. The main advantage of having a mixed reality headset in an operation theatre is its collaborative attribute. Procedures such as spatial collaboration can be conveniently done using extended reality headsets. Multiple surgeons and doctors from all around the world can join in on a surgical procedure via a platform called Dynamics 365. All of them will see the same feed and can interact with the holograms collaboratively. This takes tele surgical capabilities to a whole new level. With the successful integration and unification of mixed reality and minimally invasive surgical robotic systems, the surgical procedures carried out will be precise, fast, and reliable.

Figure 8:
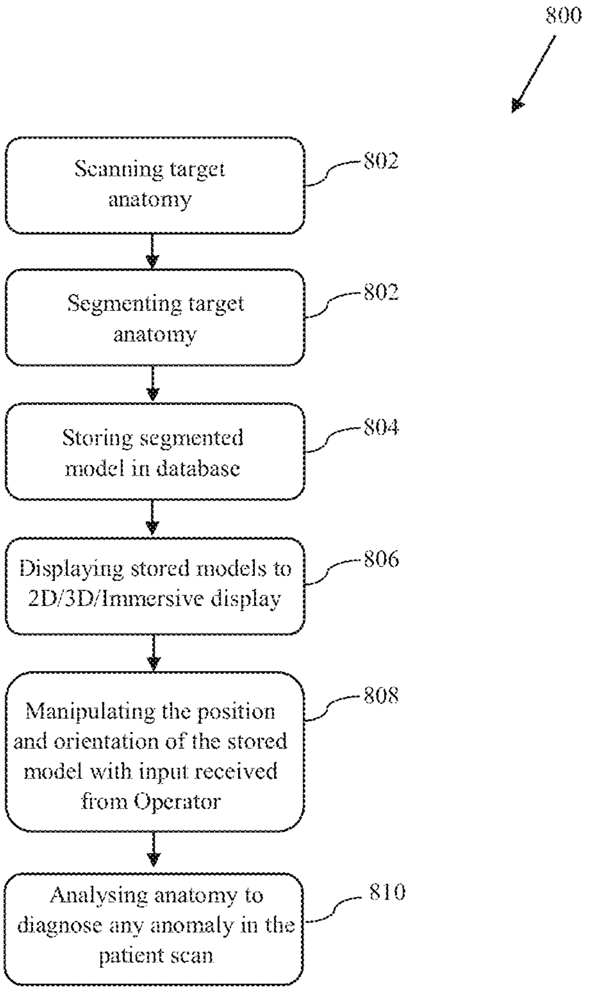
FIG. 8 illustrates a flowchart of steps followed in a pre-operative diagnosis of a target anatomy in accordance with an embodiment of the disclosure.

FIG. 8 illustrates a flowchart of steps followed in a pre-operative diagnosis of a target anatomy in accordance with an advantageous embodiment of the disclosure. In the pre-operative diagnosis, target anatomy is scanned by various scanning mechanisms, but not limited to MRI, CT, and the like. The scanned target anatomy such as DICOM files are converted in 3D type format in step (802). In step (804), the scanned target anatomy is segmented using segmentation logic as illustrated in FIG. 3, into various anatomical features but not limited to tissues, vessels, arteries, tumors, bones, and the like, depending upon the target anatomy. The segmented models of the target anatomical features are stored in a database (210) in step (806). Depending upon the requirements and interest of a particular surgery, the segmented models may be displayed to 2D monitor, 3D monitor, immersive display and the like in step (808). The position and orientation of the stored 3D model is manipulated in step (810) using the input received from the operator (204). Then, the surgeon can analyze anatomy to diagnose any anomaly in the patient diagnostic scan in step (812).

The proposed virtual reality system of the disclosure is advantageous, as it provides an economic solution for training, compared to traditional methods of training that use cadavers or dummies in an OR environment etc. The virtual training modules of the present disclosure provide interactive content, which enables visual gratification for trainees and enables greater skill retention. Also, the proposed virtual reality system of the disclosure is future forward, as the virtual reality environments are platform agnostic, so they can be used in cross platform devices making accessibility to training easier. Further, presently, there are no comprehensive training modules specific to robotic surgery in medical schools, but with the proposed virtual reality system of the disclosure, robotic surgery can be added in the curriculum making global adoption easier.

Another major advantage of the proposed virtual reality system of the disclosure, is possibility of anatomy resizing. The 3D DICOM of a virtual patient can be resized to any dimensions, making surgical planning more approachable. Further, the anatomy of the virtual patient can be super imposed on a live patient giving an x-ray vision without the necessity to have an actual x-Ray or MRI being done constantly intraoperatively. Moreover, in future, the likelihood of hosting of many web technologies in blockchain, the patient data will remain secure.

The foregoing descriptions of exemplary embodiments of the present disclosure have been presented for purposes of illustration and description. They are not intended to be exhaustive or to limit the disclosure to the precise forms disclosed, and obviously many modifications and variations are possible in light of the above teaching. The exemplary embodiment was chosen and described in order to best explain the principles of the disclosure and its practical application, to thereby enable others skilled in the art to best utilize the disclosure and various embodiments with various modifications as are suited to the particular use contemplated. It is understood that various omissions, substitutions of equivalents are contemplated as circumstance may suggest or render expedient but is intended to cover the application or implementation without departing from the spirit or scope of the claims of the present disclosure.

Benefits, other advantages, and solutions to problems have been described above with regard to specific embodiments. However, the benefits, advantages, solutions to problems, and any component(s) that may cause any benefit, advantage, or solution to occur or become more pronounced are not to be construed as a critical, required, or essential feature or component of any or all the claims.

While specific language has been used to describe the disclosure, any limitations arising on account of the same are not intended. As would be apparent to a person in the art, various working modifications may be made to the apparatus in order to implement the inventive concept as taught herein.

We claim:

1. A virtual reality system (200) for simulating a virtual robotic surgery environment comprising one or more virtual robotic arms (101*a*), (101*b*), (101*c*), (101*d*) each coupled to a virtual surgical instrument at its distal end, a virtual operating table, and a virtual patient model representing a virtual patient lying on top of the virtual operating table (103), whereby the one or more virtual robotic arms (101*a*), (101*b*), (101*c*), (101*d*) are arranged along the virtual operating table (103), the system (200) comprising:

an input device (202) configured to receive an input from an operator (204), wherein the input device (202) comprises at least one hand controller for each hand or is configured to receive hand gestures of the operator (204), and wherein the input device (202) is tracked using at least one of infra-red tracking, optical tracking using image processing, radio frequency tracking, or inertial measurement unit (IMU) sensor tracking; and a processor (206) coupled to the input device (202) and configured to:

extract a relevant data (212) based on the received input from a database (210) stored on a server (208) operably connected to the processor (206), wherein the server (208) is configured to store a database (210) including at least one of a diagnostic scan and patient details for one or more patients or a virtual tutorial for one or more robotic surgical procedures, and wherein extracting the relevant data (212) comprises fetching, based on the received input, at least one of a three-dimensional (3D) model generated from diagnostic imaging data, patient details of one or more patients, or the virtual tutorial for one or more robotic surgical procedures;

retrieve, from the database (210) stored on the server (208), patient-specific diagnostic imaging data associated with the virtual patient model, wherein the patient-specific diagnostic imaging data comprises a plurality of DICOM files generated from layer-by-layer computed tomography (CT), magnetic resonance imaging (MRI), or ultrasound scanning of the patient, each DICOM file corresponding to a cross-sectional layer of patient anatomy;

convert the retrieved diagnostic imaging data comprising one or more two-dimensional (2D) diagnostic scans into a three-dimensional (3D) anatomical model using segmentation logic, wherein the 3D anatomical model includes an anatomical organ corresponding to the virtual patient model, and wherein the segmentation logic comprises:

mapping the plurality of DICOM files into a correct layer sequence, thresholding pixel values of each layer to identify and contour anatomical structures of interest, stacking the contoured layers according to the layer mapping sequence to construct volumetric data, and generating the 3D anatomical model based on a mean volumetric value derived from the stacked pixel data;

store the 3D anatomical model as virtual patient anatomy data in the server (208);

generate an augmented three-dimensional (3D) model or a three-dimensional (3D) holographic projection of the 3D anatomical model for rendering on a stereoscopic display (214);

render the virtual robotic arms, the virtual surgical instruments, the virtual operating table, and the virtual patient model on the stereoscopic display (214), wherein the stereoscopic display (214) is coupled to a virtual reality headset or a mixed reality headset, and wherein the virtual robotic arms, the virtual surgical instruments, the virtual operating table, and the virtual patient model are rendered based on predetermined models thereof;

manipulate, based on another input received from the operator (204), the augmented 3D model or the 3D holographic projection within the virtual robotic surgery environment, wherein the manipulation comprises at least one of enlarging, rotating, filtering, slicing, or adjusting the scale of the augmented 3D model or the 3D holographic projection;

superimpose the 3D anatomical model corresponding to an anatomical organ, or the augmented 3D model or the 3D holographic projection thereof, onto the virtual patient model within the virtual robotic surgery environment at a one-to-one (1:1) scale relative to the virtual patient model; and enable, during a simulated surgical procedure, identification of a position and orientation of the anatomical organ relative to the virtual patient model based on the superimposed 3D anatomical model, the augmented 3D model, or the 3D holographic projection to enable pre-operative planning of the surgical procedure within the virtual robotic surgery environment.

2. The system as claimed in claim 1, wherein the server (208) comprises at least one of a local database (210) or a cloud-based database (210).

3. The system as claimed in claim 1, wherein each of the diagnostic scan and patient details of one or more patients and the virtual tutorial for one or more robotic surgical procedures comprises 2D images, 3D images, or both, and texts.

4. The system as claimed in claim 1, wherein storing the database (210) including the diagnostic scan and patient details comprises:

creating a database (210) of a diagnostic scan and patient details of one or more patients; and modifying the database (210) of one or more patients.

5. The system as claimed in claim 1, wherein the diagnostic scan comprises various medical scans, but not limited to magnetic resonance imaging (MRI) scan, computerized tomography (CT) scan, and the like, of one or more patients.

6. The system as claimed in claim 1, wherein the patient details comprise at least one of a name, age, sex, or medical history of one or more patients.

7. The system as claimed in claim 1, wherein storing the database (210) including a virtual tutorial for one or more robotic surgical procedures comprises:

creating a database (210) of virtual tutorials for one or more robotic surgical procedures using one or more virtual surgical instruments in a virtual robotic surgery environment; and modifying the database (210) of virtual tutorials.

8. The system as claimed in claim 1, wherein the virtual tutorials of one or more robotic surgical procedures can be used to provide training to healthcare professionals.

9. The system as claimed in claim 1, wherein extracting the relevant data (212) from the stored database (210) on the server (208) comprises fetching at least one of a 3D model of diagnostic scan and patient details of one or more patients, or a virtual tutorial for one or more robotic surgical procedures, based on the received input.

10. The system as claimed in claim 1, wherein the relevant data (212) comprises augmented 3D model or a 3D holographic projection, related to at least one of a diagnostic scan and patient details of one or more patients, or a virtual tutorial for one or more robotic surgical procedures.

11. The system as claimed in claim 1, wherein rendering the relevant data (212) comprises displaying the augmented 3D model on a stereoscopic display (214).

12. The system as claimed in claim 11, wherein the rendered image can be projected on an external display (216).

13. The system as claimed in claim 1, wherein the stereoscopic display (214) is coupled to a virtual reality headset.

14. The system as claimed in claim 1, wherein the 3D models of diagnostic scan and patient details of one or more patients can be stored on the server for safekeeping and reference.

15. The system as claimed in claim 1, wherein the 3D model of a diagnostic scan can be manipulated to diagnose any anomalies in the diagnostic scan of one or more patients.

16. The system as claimed in claim 1, wherein the 3D models of diagnostic scan and patient details of one or more patients can be used for training healthcare professionals.

17. The system as claimed in claim 1, wherein the manipulated data comprises a modified version of the relevant data (212), generated based on the received input from the operator (204).

18. The system as claimed in claim 1, wherein rendering the relevant (212) data of a virtual tutorial for a selected robotic surgical procedure, based on the received input comprises of following steps:

positioning of the virtual patient on the virtual operating table;

placing of virtual ports on the virtual patient;

draping of the virtual robotic arms;

docking of the virtual robotic arms in the patient around the virtual operating table;

selecting one or more virtual surgical instruments;

practicing the selected surgical procedure by using the virtual surgical instruments;

undocking and storing the virtual robotic arms;

practicing quick undocking of the virtual robotic arms in case of any adverse situation; and cleaning and sterilizing of the virtual surgical instruments post the virtual surgical procedure.

19. The system as claimed in claim 1, wherein the processor (206) is further configured to transmit the manipulated data to the server (208) for storage in the database (210).

20. The system as claimed in claim 1, wherein simulating the virtual robotic surgery environment is based on predetermined models for the virtual robotic arms, the virtual surgical instruments, the virtual operating table, and the virtual patient.

21. The system as claimed in claim 1, wherein separate sessions of the virtual tutorials for surgeons and operation theater (OT) staff can be designed using the virtual robotic surgery environment.

22. A method for simulating a virtual robotic surgery environment comprising one or more virtual robotic arms each coupled to a virtual surgical instrument at its distal end, a virtual operating table, and a virtual patient model representing a virtual patient lying on top of the virtual operating table, whereby the one or more virtual robotic arms are arranged along the virtual operating table, the method comprising:

receiving, using an input device (202), an input from an operator (204), wherein the input device (202) comprises at least one hand controller for each hand or is configured to receive hand gestures of the operator (204), and wherein the input device (202) is tracked using at least one of infra-red tracking, optical tracking using image processing, radio frequency tracking, or inertial measurement unit (IMU) sensor tracking;

storing, using a server (208), in a database (210) at least one of a diagnostic scan and patient details for one or more patients or a virtual tutorial for one or more robotic surgical procedures;

extracting, using a processor (206), a relevant data (212) based on the received input, from the database (210) stored on the server (208), wherein extracting the relevant data (212) comprises fetching, based on the received input, at least one of a three-dimensional (3D) model generated from diagnostic imaging data, patient details of one or more patients, or the virtual tutorial for one or more robotic surgical procedures;

retrieving, from the database (210) stored on the server (208), patient-specific diagnostic imaging data associated with the virtual patient model, wherein the patient-specific diagnostic imaging data comprises a plurality of Digital Imaging and Communications in Medicine (DICOM) files generated from layer-by-layer computed tomography (CT), magnetic resonance imaging (MRI), or ultrasound scanning of the patient, each DICOM file corresponding to a cross-sectional layer of patient anatomy;

converting, using the server (208), the retrieved patient-specific diagnostic imaging data comprising one or more two-dimensional (2D) diagnostic scans into a three-dimensional (3D) anatomical model by applying segmentation logic, wherein the 3D anatomical model includes an anatomical organ corresponding to the virtual patient model, and wherein the segmentation logic comprises:

mapping the plurality of DICOM files into a correct layer sequence;

thresholding pixel values of each layer to identify and contour anatomical structures of interest;

stacking the contoured layers according to the layer mapping sequence to construct volumetric data; and generating the 3D anatomical model based on a mean volumetric value derived from the stacked pixel data;

storing, using the server (208), the 3D anatomical model as virtual patient anatomy data;

generating, using the processor (206), an augmented three-dimensional (3D) model or a three-dimensional (3D) holographic projection of the 3D anatomical model for rendering on a stereoscopic display (214);

rendering, using the processor (206), the virtual robotic arms, the virtual surgical instruments, the virtual operating table, and the virtual patient model on the stereoscopic display (214), wherein the stereoscopic display (214) is coupled to a virtual reality headset or a mixed reality headset, and wherein the virtual robotic arms, the virtual surgical instruments, the virtual operating table, and the virtual patient model are rendered based on predetermined models thereof;

manipulating, using the processor (206), based on another input received from the operator (204), the augmented 3D model or the 3D holographic projection within the virtual robotic surgery environment, wherein the manipulation comprises at least one of enlarging, rotating, filtering, slicing, or adjusting the scale of the augmented 3D model or the 3D holographic projection;

superimposing, using the processor (206), the 3D anatomical model corresponding to the anatomical organ, or the augmented 3D model or the 3D holographic projection thereof, onto the virtual patient model within the virtual robotic surgery environment at a one-to-one (1:1) scale relative to the virtual patient model; and enabling, during a simulated surgical procedure, identification of a position and orientation of the anatomical organ relative to the virtual patient model based on the superimposed 3D anatomical model, the augmented 3D model, or the 3D holographic projection to enable pre-operative planning of the surgical procedure within the virtual robotic surgery environment.

23. The method as claimed in claim 22, wherein simulating the virtual robotic surgery environment is based on predetermined models for the virtual robotic arms, the virtual surgical instruments, the virtual operating table, and the virtual patient.

* * * * *